US008769913B2

(12) United States Patent
Monti

(10) Patent No.: US 8,769,913 B2
(45) Date of Patent: *Jul. 8, 2014

(54) METHOD AND AN APPARATUS FOR TRANSFERRING FRAGILE RECEPTACLES FROM A CONTAINER TO A PACKING MACHINE

(75) Inventor: Giuseppe Monti, Pianoro (IT)

(73) Assignee: Marchesini Group S.p.A., Pianoro (BO) (IT)

( * ) Notice: Subject to any disclaimer, the term of this patent is extended or adjusted under 35 U.S.C. 154(b) by 160 days.

This patent is subject to a terminal disclaimer.

(21) Appl. No.: 13/272,665

(22) Filed: Oct. 13, 2011

(65) Prior Publication Data

US 2012/0093618 A1 Apr. 19, 2012

(30) Foreign Application Priority Data

Oct. 14, 2010 (IT) .............................. BO2010A0615

(51) Int. Cl.

| | |
|---|---|
| ***B65B 5/08*** | (2006.01) |
| ***B65B 35/36*** | (2006.01) |
| ***A61M 5/00*** | (2006.01) |
| ***B65G 47/90*** | (2006.01) |
| ***B65B 23/22*** | (2006.01) |

(52) U.S. Cl.

CPC ............ *B65G 47/902* (2013.01); *B65G 47/907* (2013.01); *B65B 5/08* (2013.01); *B65B 23/22* (2013.01); *B65B 35/36* (2013.01); *A61M 5/008* (2013.01)

USPC .................... 53/444; 53/473; 53/148; 53/251

(58) Field of Classification Search

CPC ......... A61M 5/008; B65B 5/08; B65B 23/22; B65B 35/36; B65G 47/902; B65G 47/907

USPC ........... 53/147, 148, 142, 244, 246, 247, 544, 53/539, 443, 444, 446, 473, 475, 492, 53/381.1

See application file for complete search history.

(56) References Cited

U.S. PATENT DOCUMENTS 3,133,635 A * 5/1964 Gordon et al. ................ 206/366
4,456,115 A * 6/1984 McKnight et al. ........ 198/377.03

(Continued)

FOREIGN PATENT DOCUMENTS

DE 3409225 A1 * 9/1985 ............. B65B 23/22
DE 4102618 A 8/1992

(Continued)

OTHER PUBLICATIONS

European Search Report for EP 2441711, Dated Dec. 12, 2011, 2 pages.

*Primary Examiner* — Stephen F Gerrity
(74) *Attorney, Agent, or Firm* — William J. Sapone; Ware Fressola; Maguire & Barber LLP

(57) ABSTRACT

A method and an apparatus (A) are disclosed, for transferring a plurality of tubular receptacles (1) made of a fragile material, suitable for containing doses of medicinal substances, for example barrels (1) for syringes or vials, from containers (2, 20), in which the receptacles (1) are housable separated from one another, to a packing machine (M) for processing the receptacles (1). Each container (2, 20) houses a multiplicity of receptacles (1) and is transportable by a conveyor line (L) towards the packing machine (M). The method includes the following steps: a. collecting a plurality of receptacles (1) from a container (2, 20), maintaining the receptacles (1) separated from one another; b. arranging the collected receptacles (1) at an inlet (I) of the packing machine (M), in a predefined formation and kept separated from one another, and c. bringing the receptacles (1), collected and arranged in the preceding steps, into the packing machine (M), maintaining them separated from one another, so that the packing machine (M) can receive and process them.

14 Claims, 9 Drawing Sheets

(56) References Cited

U.S. PATENT DOCUMENTS

| | | | | |
|---|---|---|---|---|
| 7,229,110 | B1 * | 6/2007 | Tye | 294/87.1 |
| 7,421,833 | B2 * | 9/2008 | Rothbauer et al. | 53/471 |
| 2001/0045081 | A1 * | 11/2001 | Aylward | 53/244 |
| 2003/0009994 | A1 * | 1/2003 | Hartness et al. | 53/473 |
| 2005/0097863 | A1 * | 5/2005 | Taggart | 53/167 |
| 2005/0133729 | A1 * | 6/2005 | Woodworth et al. | 250/455.11 |
| 2006/0191240 | A1 | 8/2006 | Rothbauer et al. | |
| 2008/0283370 | A1 * | 11/2008 | Monti | 198/867.01 |
| 2009/0067973 | A1 * | 3/2009 | Eliuk et al. | 414/729 |
| 2009/0288973 | A1 * | 11/2009 | Hesseldahl | 206/366 |
| 2010/0139215 | A1 * | 6/2010 | Van Roy | 53/444 |
| 2010/0243501 | A1 * | 9/2010 | Monti | 206/446 |

FOREIGN PATENT DOCUMENTS

| | | | | | |
|---|---|---|---|---|---|
| DE | 29922962 | U1 * | 3/2000 | A61M 5/008 |
| DE | 102004035061 | A | 2/2006 | |
| EP | 0460134 | B1 * | 9/1993 | B65B 23/22 |
| EP | 0488946 | B1 * | 10/1994 | B65G 47/902 |
| EP | 1842807 | A1 * | 10/2007 | B65G 47/907 |
| EP | 2196395 | A | 6/2010 | |

* cited by examiner

METHOD AND AN APPARATUS FOR TRANSFERRING FRAGILE RECEPTACLES FROM A CONTAINER TO A PACKING MACHINE

FIELD OF THE INVENTION

The present invention relates to methods and apparatus for transferring fragile articles from a supply line and feeding them to a machine for processing the items.

In particular, the invention relates to methods and apparatus used to transfer, for packing, syringe barrels or vials, tubes or other small receptacles made of fragile material, such as glass, and particularly designed to contain liquids or other loose substances.

DESCRIPTION OF THE PRIOR ART

In the following, for ease of description, reference will be made, purely by way of example, to the problem of transferring glass barrels, which constitute the well-known tubular body of syringes, for containing a liquid to be injected from a supply line to a packing machine that processes them such as to pack the relative syringes (such as for example a piston-inserting and a labeling machine).

The barrels, for example, already filled and sealed with rubber caps, usually known as "rubber stoppers", inserted into the upper mouth thereof, reach the packing machine housed in a special container transported by the conveyor line.

There are two main types of container, well known in the field, which are designed to accommodate tubular glass barrels.

The first type consists of the so-called "nest", so called because they resemble wasps' nests, which have a grid shape and can house a plurality of vertical glass barrels, each within a respective "cell", or housing, comprising a through- and vertical cavity.

In detail, the cells, and the barrels housed in them, are arranged in the nest and spaced along parallel lines.

In practice, when they are housed in the nest, the barrels are not in contact with each other, and rest on the edge of the cavity of the relative housing by means of a small support collar conformed from the edge of the mouth thereof, designed to accommodate the plunger of the future syringe when finished.

The bottoms of the barrels protrude inferiorly from the cell and the nest.

The other known type of container is constituted by trays in which each body is housed horizontally in a respective seating conformed, for example, as a complementary impression of the body itself, which is superiorly accessible.

In this case too the seatings are arranged in the tray so that the barrels are housed in several parallel rows and not in contact with each other.

The known process for transferring the barrels from the container to the packing machine is explained below.

A plurality of barrels to be transferred, via various devices known in the field are simultaneously removed from the container in which they are housed.

This is because it is clear that collecting only one body at a time would obviously have a detrimental effect on performance, causing a so-called "bottleneck" in the receiving, packaging and packing chain of the syringes.

Subsequently, the barrels are arranged in a directing guide located at the inlet of the packing machine such as to supply the machine, which guide is configured such that the barrels travel to the interior of the packing machine in single file in contact with one another.

In fact, the barrels must be supplied to the packing machine arranged in a predefined formation and then are appropriately directed.

Normally, the guide is composed of two wire tracks on which the barrels slide, resting on the support collars thereof, as described above.

The experience of using this procedure and its means of implementation has brought to light the drawback which is described below.

Once the barrels have been taken from the nest, or alternatively from the tray, and have been inserted in the guide, they are often subject to colliding with each other during their directing towards the packing machine.

Since syringe barrels are made of a fragile material, impacts are often the cause of cracks and/or chipping, if not shattering.

This causes low yields and high costs.

SUMMARY OF THE INVENTION

The aim of the present invention is to obviate the above-described drawback and others by means of:

a method for transferring a plurality of tubular receptacles made of a fragile material, suitable for containing doses of medicinal substances, for example barrels for syringes or vials, from containers in which the receptacles are housable separately, to a packing machine for processing the receptacles (1), and an apparatus for performing the method, in accordance with the invention.

The method comprises the following steps:

a. collecting a plurality of receptacles from a container, maintaining the receptacles separated from one another, b. arranging the collected receptacles at an inlet of the packing machine, in a predefined formation in which they are kept separated from one another, and c. bringing the receptacles, collected and arranged in the preceding steps, into the packing machine, maintaining them separated from one another, whereby the packing machine can receive them, once they have entered therein, so as to process them.

The apparatus comprises:

at least one pick-up means for picking up a plurality of receptacles at a time from a container and releasing the receptacles, once picked up;

at least one inserting device provided at the inlet of the packing machine, for bringing the receptacles extracted from the container to the inlet of the packing machine, where they are collected, and a displacing means for supporting the pick-up means and displacing the pick-up means, once the pick-up means have picked up the receptacles, so that the picked-up receptacles are extracted from the container and are then taken to the inserting device.

Further, in the apparatus according to the invention, it is provided that:

the inserting device comprises a plurality of movable seatings arranged separated from one another, each being suitable for housing a receptacle, in such a way that the housed receptacles are arranged in a predefined configuration in which they are separated from one another, the inserting device being further activatable to move the movable seatings, with the receptacles housed therein, such that the receptacles are brought to the inlet of the packing machine;

the pick-up means being configured so as to maintain the receptacles separated while picking them up and once they are picked-up; and wherein the displacing means (4) is activatable to displace the pick-up means, once the pick-up means have picked up the receptacles, up to the inserting device, and to move the pick-up means so that the receptacles are introduced in relative movable seatings of the inserting device, whereby, once the pick-up means have released them, they are transported thereby.

In the following, we will refer to a special case in which the receptacles relate to syringe barrels, but it goes without saying that this choice, unless it is specified otherwise, is purely for descriptive purposes and does not limit the field of application of the invention.

Whether the barrels are brought into the packing machine in nests or in trays, they are however transported separated from each other, as explained above, and therefore they cannot in any way impact against one another.

Using the proposed method and/or the apparatus, the barrels are extracted from the receptacles in which they are housed, keeping them separated from each other.

The expression "separated" in this context clearly indicates physically separate, i.e. not in contact and in any case sufficiently spaced so that normal vibrations and oscillations occurring during the movements caused by devices and machines do not cause collision between the barrels.

Thereafter the barrels are moved up to be placed in proximity of or at the inlet of the packing machine.

During this movement, as duly set out herein, the barrels are always maintained separated, such that the possibility of mutual collision is entirely prevented.

At this point, the barrels are arranged in a predefined formation suitable for inserting in the inlet of the packing machine.

In fact, as already explained above, it is clear that the packing machine can take delivery and then process the barrels if they are supplied into the inlet configuration comprised in the constructional specifications of the machine, which can vary from machine to machine.

Even in the predefined formation, the barrels are maintained separated.

Finally, the barrels are brought to the inlet of the packing machine, keeping them separate during this final transport, such that the packing machine may take delivery of them and process them in the intact condition.

In this way, the risks and costs that beset the above-described prior art are completely prevented.

BRIEF DESCRIPTION OF THE DRAWINGS

Specific embodiments of the invention, and advantageous technical-functional characteristics related to these embodiments only partly derivable from the description set out above, will be described in the course of the description, in accordance with what is set out in the claims and with the aid of the attached figures of the drawing, in which:

DESCRIPTION OF THE PREFERRED EMBODIMENTS

Figure 1A:
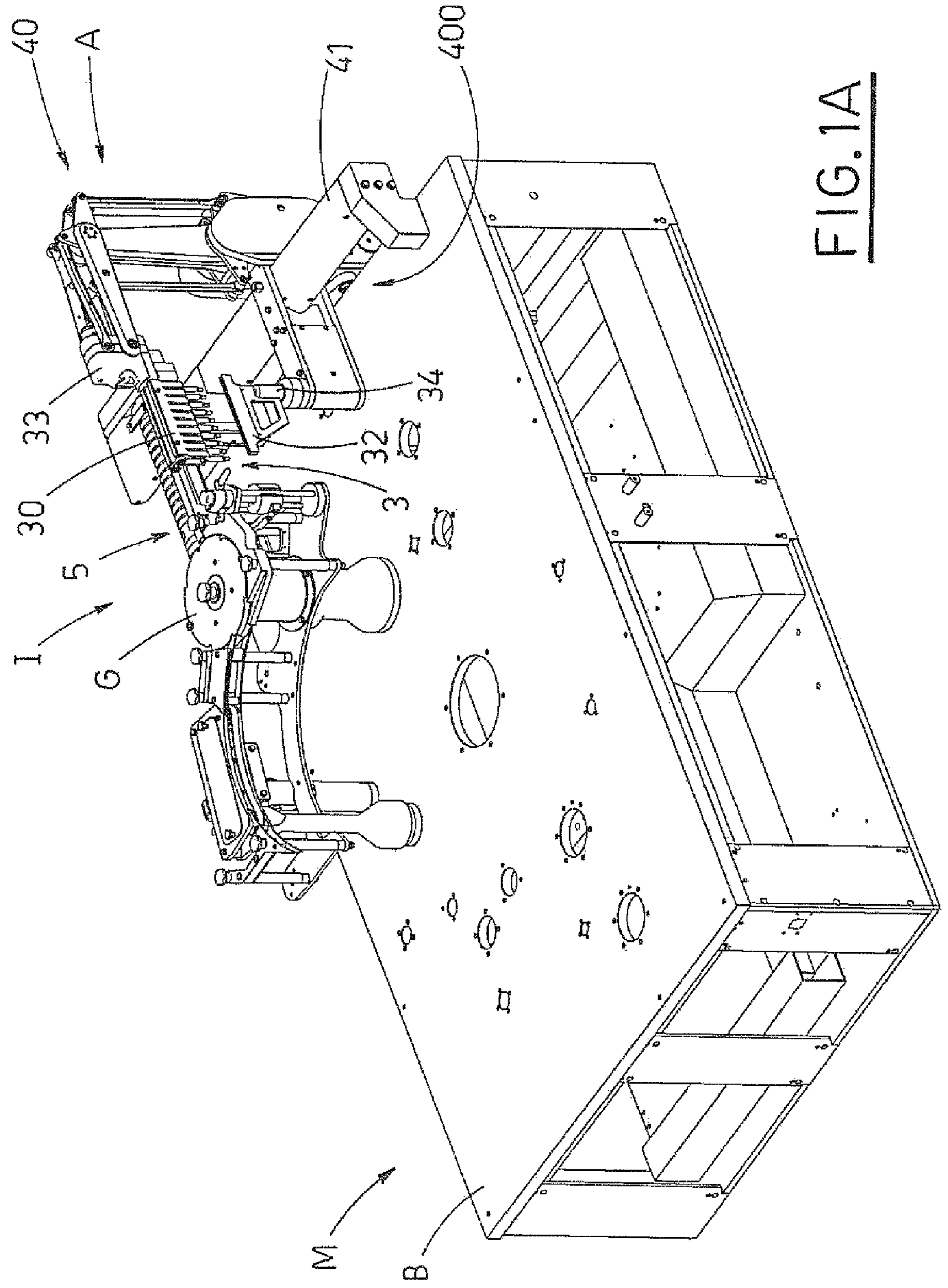
FIG. 1A is an axonometric projection apparatus according to the invention associated with a bench of a packing machine, not represented, apart from the Archimedes screw located just inside the inlet of the machine.
Figure 1B:
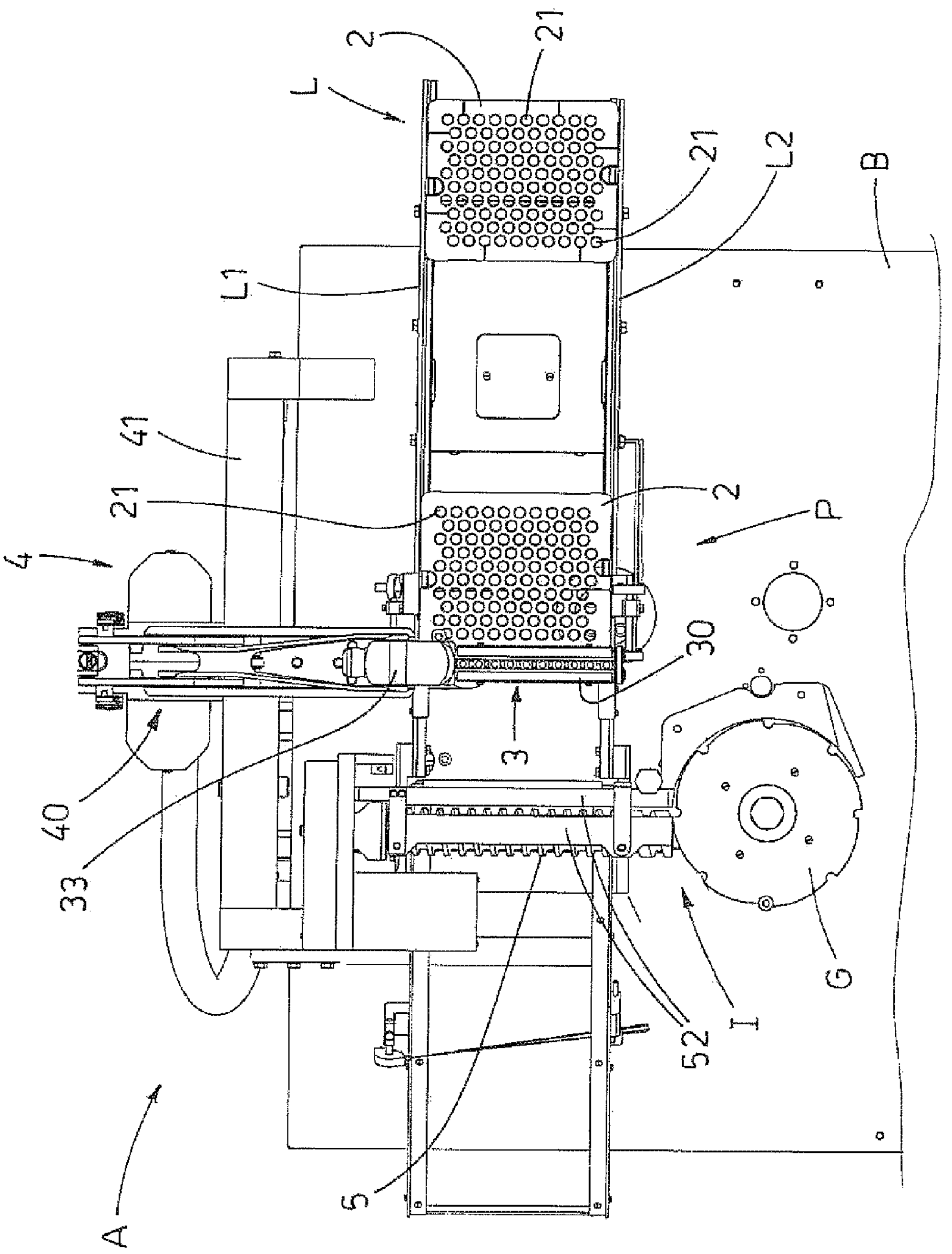
FIG. 1B is a partial view from above of the illustration 1A, also showing a conveyor line of the receptacles housing the receptacles.

FIGS. 1A and 1B illustrate the apparatus associated with the disclosed packing machine M, with the entrance I thereof immediately just inside the machine M, and a carousel G, in a known way, destined to take delivery of each receptacle 1 that enters the machine M.

Clearly, the representation G of the carousel in the drawings should be viewed as an aid to the understanding of the invention, as the machine M could be of any type suitable for the processing of receptacles 1 (and in fact, apart from the carousel G and the bench B, the machine M is not further illustrated in the attached figures).

The apparatus A in possible embodiments thereof will be described in detail after having explained some possible variants of the method of the invention.

As already mentioned above, the method is applicable to a case where the barrels are "barrels" for syringes 1.

In the accompanying figures only receptacles 1 in the form of barrels are illustrated.

The barrels 1, as mentioned, are suitable receptacles for containing liquid to be injected, each comprising an upper support collar 10 conformed by a rim of a respective mouth.

Further, each barrel 1 has a closed bottom opposite the mouth 11 and a lateral wall 100 joining the support collar 10 to the bottom 11.

In the case shown in the figures, the bottom 11 is conformed by the barrel 1 itself. However, it is possible that the barrels 1, already bearing the needle that projects from the bottom, might be coupled to a lower safety element in which the needle is completely buried, which safety element forms the bottom 11, which in this case can be fully closed, and which of course is opposite the entrance mouth of the body 1.

In the following generic reference will be made to the 'bottom 11 of a body 1', in reference also to the case of a presence of the safety element.

That said, each of these receptacles may include a nest for 2 barrels 1, which nest 2 in turn includes a plurality of separate housings 21, each comprising a vertical through-cavity for accommodating a respective body 1 (i.e. provided with the vertical development arranged vertically), resting on a top edge 210 of the cavity with the support collar 10 thereof, and with the respective bottom 11 projecting inferiorly of the nest 2.

The housings 21 are arranged together so that the housed barrels 1 are separated from one another.

Figure 4:
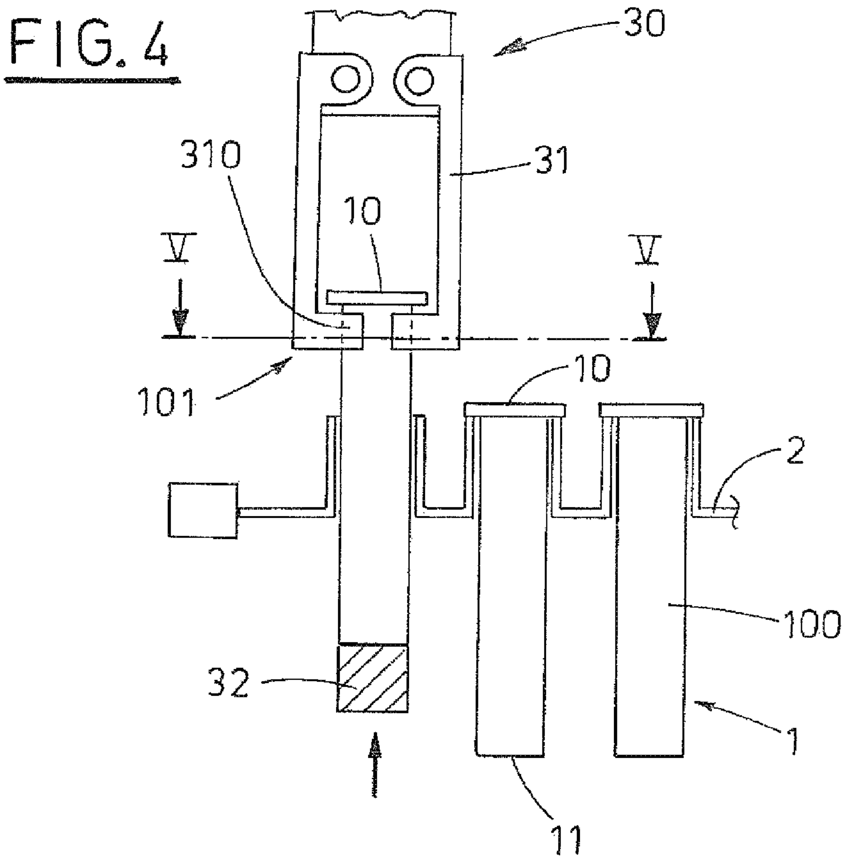
FIG. 4 is the same view as the previous figure, in which the receptacles have been raised and gripped by pliers included in pick-up and place means.

In a first variant of the method, steps a, b and c are respectively implemented by phases a', b' and c' as follow:

a'. plurality of barrels 1 receive an upwardly-directed push impressed on the bottom 11 thereof (as illustrated in FIG. 4, the pusher means mentioned here will be described herein below), which pusher causes a respective upper part 101 comprising the support collar 10 to project superiorly of the relative housing 21 and thus the nest 2; following which, each of the barrels 1 thrust upwards is picked up by the projecting upper part 101 thereof and is then removed from the housing 21, and is thus removed from the nest 2 while being maintained separated from the other barrels 1 that have been picked up;

b'. the barrels 1 which have been picked up are brought to the inlet I of the packing machine M and arranged in a line, separated from one another, the line constituting the predefined formation (in this way, for example, the method is adaptable to the presence of a carousel G, as explained herein above), and c'. the line of barrels 1 is longitudinally translated such as to bring the barrels 1 one at a time into the packing machine M, maintaining the barrels 1 separated from one another during the translation.

This variant of the method is devised precisely for the case where the barrels 1 are supplied in a nest 2.

In fact, this variant advantageously uses the same concept as the nests 2 housing (the bottom 11 of the barrels 1 projecting inferiorly, barrels resting freely on the collar 10, etc. . . . ) in order to pick up and then transport the barrels so that 1 the possibility of reciprocal colliding is completely prevented.

As mentioned earlier, the housings 21, and therefore the barrels 1 are usually arranged in parallel rows in the nests 2.

Further, the nests 2 can be powered by the conveyor line L in a row up to a pickup position P, near the inlet of the packing machine M, where the nests 2 of the row halt during the pick-up operations (see FIG. 1B).

In practice, the conveyor line L can be configured such as to have nests 2 in single file "in step" with the nests 2 themselves which stop one at a time at the pick-up position P, up until all the barrels housed therein have been collected.

Thereafter, the nest 2, emptied of barrels 1, is moved from the pickup position P (and unloaded, as will be seen) and the line L is activated to bring a further nest 2 into the pick-up position.

The conveyor line may be formed by two tracks L1, L2 (see FIG. 1B) arranged flanked to the nest 2, which is between them, the tracks L1, L2, supporting the nest 2, which are supported by opposite lateral edges thereof, which in turn flank the assembly of housings 21 arranged centrally in the nest 2, such as to leave space above and below the nest in 2, which is then accessible from both above and below.

Figure 10:
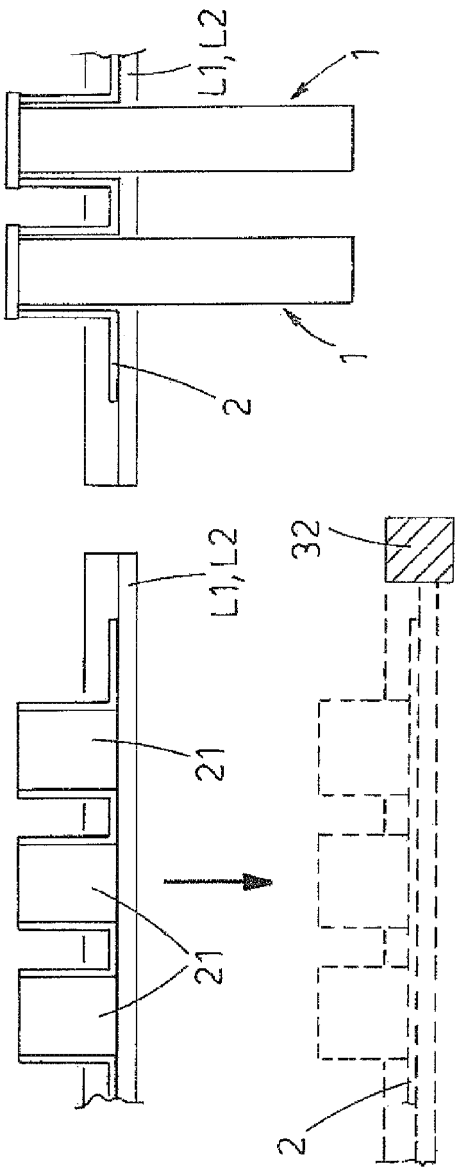
FIGS. 10 and 11 show an eliminating cycle of an empty nest.
Figure 11:
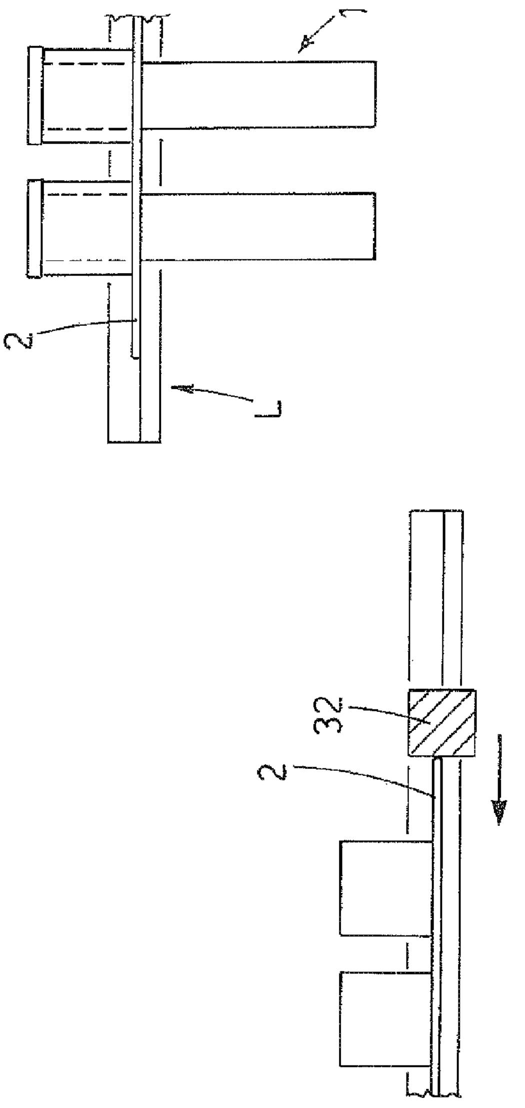
Figure 11:
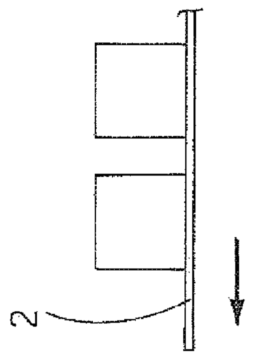

With this in mind, in a second variant of the method:

step a' is carried out by applying it to the barrels 1 of a whole line of housings 21 of the nest 2 which is in the pick-up position P;

during step b', the line of barrels 1 picked up during step a' is arranged with all the barrels 1 maintained vertical such that the support collar 10 and the mouth are arranged superiorly and the bottom 11 inferiorly, in said line at the inlet I of the packing machine M, after which step c' is carried out;

steps a', b' and c' are repeated by applying them cyclically to each of the parallel lines of barrels 1 housed in the nests 2 and are carried out such that step c' has a duration which is at most equal to a sum of durations of step a' and step b', such that step c' of a cycle relating to a line of barrels 1 can be completed during steps a' and b' applied to a further line of barrels 1 in the following cycle; and after all the barrels 1 which were housed in the nest 2 present in the pick-up position P have been removed, the nest 2 is removed from the conveyor line L (and in the following it will be explained how, with the aid of FIGS. 10 and 11), which advances a further nest 2 up to the pick-up position P and the steps of the method are repeated from the beginning for as long as nests 2 containing barrels 1 to be picked up are supplied.

This second variant of the method enables the maximum pick-up efficiency or, differently expressed, the greatest time saving for the pick-up, without in any way changing the fact that, as in all variants of the method, the receptacles 1 arriving at the machine M have never collided with one another.

In addition, this variant enables the barrels 1 to be presented to the packing machine M already vertically arranged with the mouth thereof facing upwards, such that they are already predisposed in such a way that the machines today available on the market can insert the rod of the plunger of the syringe, for example, or fill the syringes with the liquid to be injected, if they are still empty, etc.

Figure 12A:
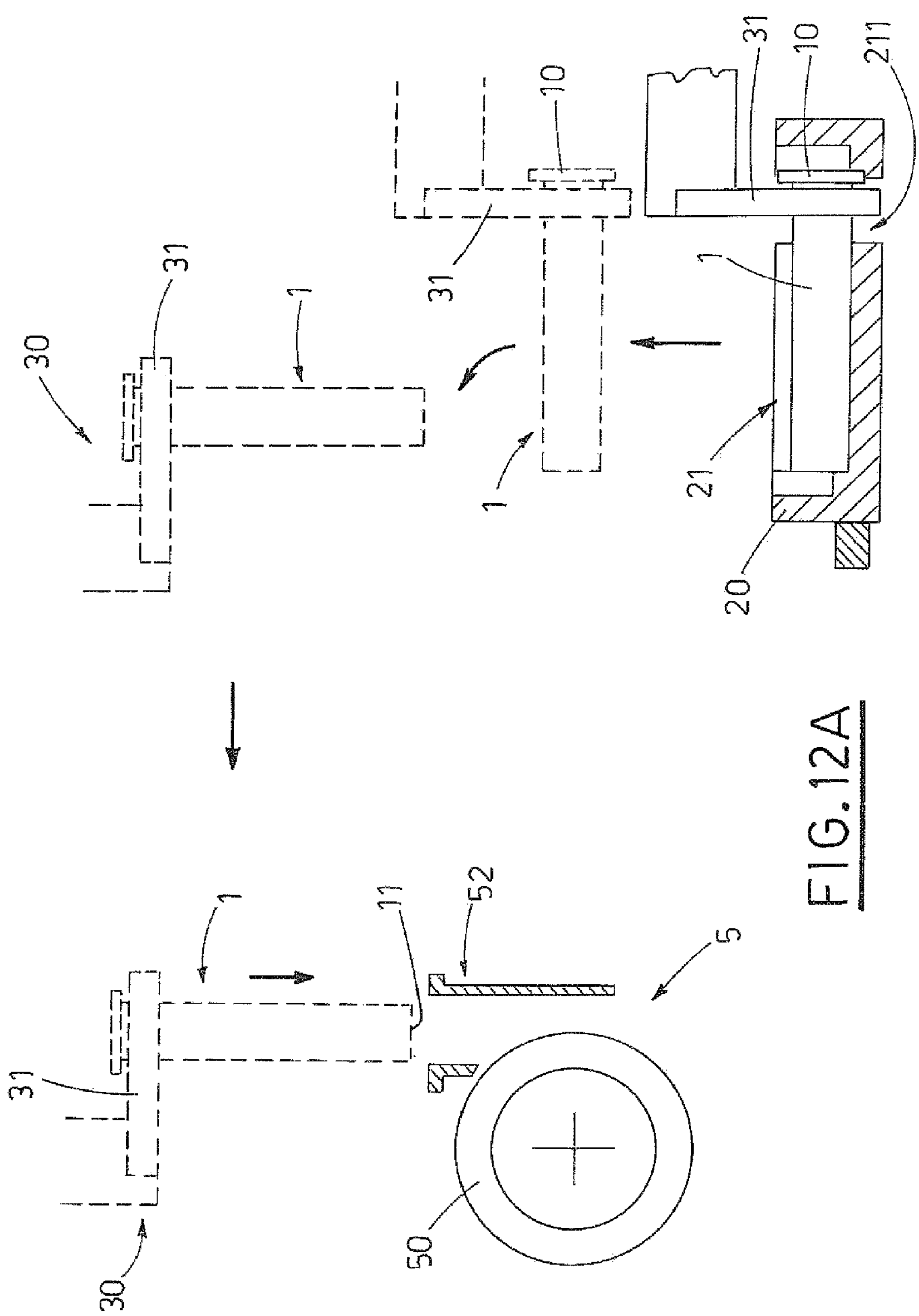
FIGS. 12A and 12B are schematic views illustrating the functioning of the apparatus when used with so-called "trays".
Figure 12B:
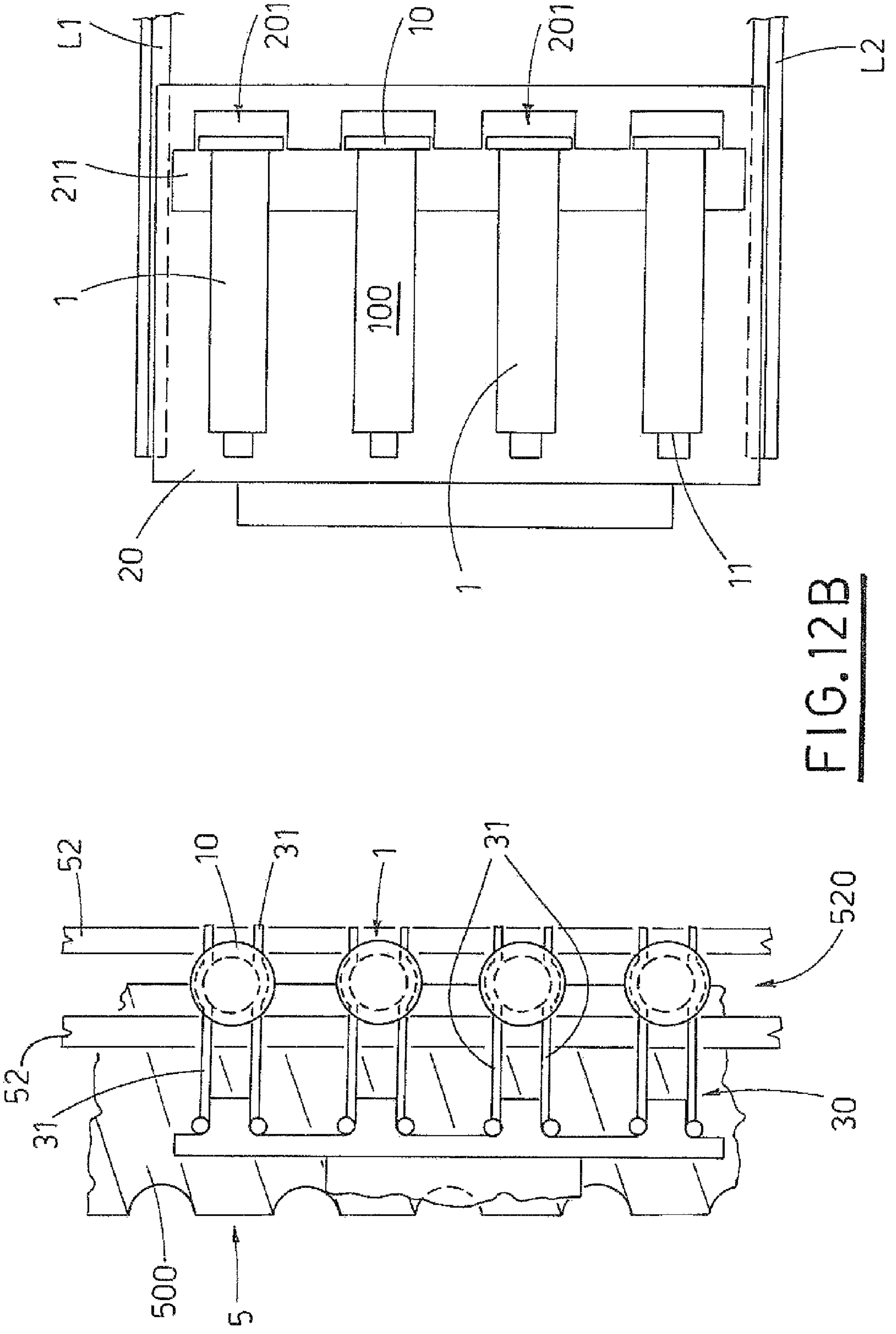

A further variant of the method is comprised for a case in which each receptacle comprises a tray 20 in turn comprising a plurality of housings 201, superiorly open such as to accommodate the individual receptacles 1 lying horizontally (i.e. with the longitudinal development arranged horizontally), and such that they are separated from each other (see FIG. 12B).

As explained herein above, in this tray 20, of known type, the housings 201 normally have a substantially complementary shape with respect to the receptacle 1 in a laid-down position, with the possibility of some extra space for the use of drawing means, as will be explained in detail later.

In this case, the phases a, b and c are respectively implemented by steps a ', b' and c' as follows (not coinciding with the same steps outlined above with reference to illustrated variants):

a'. a plurality of receptacles 1 are lifted from the respective housing 201 up to picking them up from the tray 20, such that they are maintained separated from one another, b'. the picked up receptacles 1 are then taken to the inlet I of the packing machine M and arranged in a line, separated from one another, the line constituting said predefined formation; and c'. the line of receptacles 1 is translated longitudinally such as to bring the receptacles 1 one at a time into the packing machine M, constantly keeping the receptacles 1, during the translation, separated from one another.

This variant exploits the superior accessibility of the housings 201.

As mentioned above, in the trays 20 of this type the housings 201, and the vessels placed in them, may also be arranged in parallel rows in the trays 20.

In detail, the parallel rows of housings 201 can be intercalated between them to save space.

Clearly, the trays 20 may be supplied from the conveyor line L in a row to the pick-up position P, where they stop during the drawing operations, similarly to the case where nests 2 are used.

In this case, a variant of the method can be actuated, in which:

step a. is carried out by applying it to a whole line of receptacles 1 of the tray 20 which is in the pick-up position P, lifting all the line vertically and contemporaneously from the tray 20;

during step b'. the line of receptacles 1 picked up during stage a'. is rotated such that all the receptacles 1 are arranged vertically, and the rotated line of receptacles 1 is arranged in the line formation at the inlet I of the packing machine M, after which step c'. is actuated;

steps a', b' and c' are repeated by applying them cyclically to each of the parallel lines of the receptacles 1 housed in the tray 20 and are carried out such that step c' has a duration which is at most equal to the sum of the durations of step a. and step b'., so that step c' of a cycle relating to a line of receptacles 1 can be completed during steps a' and b', applied to a further line of receptacles 1 in a following cycle; and after all the receptacles 1 which were housed in the tray 20 in the pick-up position P have been collected, the tray 20 is removed from the conveyor line L, which advances a further tray 20 up to the pick-up position P and the steps of the method are repeated from the beginning.

The two possible variants of the method described above, and relating to the case of receptacles involving use of the trays 20, are applicable to the transfer of barrels 1 of the kind already described several times.

In this case, during step c. (and therefore also possibly step c'), the barrels 1 themselves can be arranged with the support collar 10 and the mouth placed superiorly and the bottom 11 placed inferiorly, for the reasons discussed above.

Figure 9:
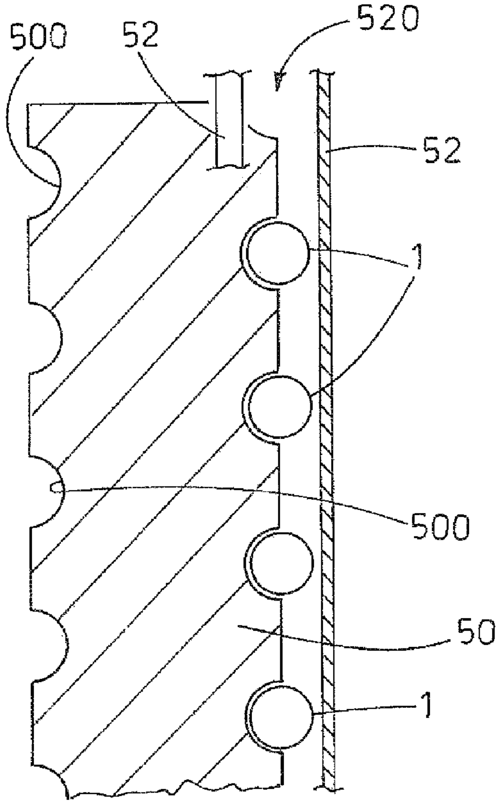
FIG. 9 is a horizontal section view of FIG. 8 taken along plane IX-IX.

According to a further possible aspect of the method according to the invention, a plurality of movable seatings 51 are made available at the inlet I of the packing machine M (reference is made to FIG. 7 and FIG. 9) each for housing a relative receptacle 1 and for transporting the receptacles 1 housed therein to and into the inlet I of the packing machine M.

A preferred embodiment of the movable seatings 51 will be described herein below, when the proposed apparatus A is described.

In the just-described special detail, during step c, the movable seatings 51 are arranged with respect to one another such that the receptacles 1, once inserted in the movable seatings 51, are moment by moment in the above-mentioned formation, in which they are separated from one another; further, the movable seatings are moved continuously, and finally during step b the receptacles 1 are placed in movable seatings 51 in follow-mode, while they are moving.

The above-described is an embodiment in which the certainty of insertion of the receptacles in the machine M without colliding is obtained while performance is also maximized.

As specified above, the apparatus A comprises (once more in reference to FIGS. 1A and 1B), the pick-up means 3, an inserting device 5 (shown for example in FIGS. 6 and 7, and described in detail below), and the displacing means 4 (shown only in FIGS. 1A and 1B).

The inserting device 5 advantageously comprises the above-mentioned plurality of movable seatings 51, configured and activatable as described herein above.

The pick-up means 3 may include (as seen in FIGS. 2, 3, 4, 5 and 12, for example) a plurality of pliers 30 arranged above the receptacle 2, 20 (see FIGS. 2 and 3), each individually closable such as to singly grip a receptacle 1, or alternatively openable such as to release the receptacle 1.

The apparatus A can be used in the case receptacles 2, 20 step-supplied by the above-mentioned conveyor line L to the pick-up position P, where they halt during the cycles of collecting and transfer of the receptacles 1 to the inserting devices 5.

For the sake of brevity, this possible operation is not repeated in the following each time a given variant of the apparatus A is described.

The pliers 30 are advantageously arranged at a mutual distance such that the receptacles 1, while gripped by respective pliers 30, are maintained separated from one another.

More specifically, the pliers 30 can each comprise a pair of jaws 31 for tightly clamping the syringes 2 (as shown in FIGS. 3, 4, 6 and 12A and 12B, for example).

Each pair of jaws 31 is clearly reciprocally rotatable with respect to a rotation axis, alternately opening out when the pliers 30 is opened, or nearing, when the pliers 30 close.

In the case of receptacles each comprising a corresponding nest 2, in the preferred embodiment of the apparatus A the pick-up means 3 includes at least a pusher element 32, arrangeable below the nest 2 and comprising an upper abutting surface 320; the pusher element 32 can oscillate vertically, such that when performing an upwards run it can push, with its upper surface 320, the bottom 11 of a row of barrels 1 in the nest 2, with the result that in the pushed barrels 1, a respective upper part 101 comprising the support collar 10 projects superiorly of the housing 21, and then to the nest 2 (with reference to FIG. 4).

Further, in this case the apparatus A also comprises that the plurality of pliers 30 is arrangeable above the nest 2 (FIGS. 3 and 4), and each of the relative pairs of jaws 31 is closed such as to clamp one of the barrels 1 pushed upwards by the pusher element 32, gripping the protruding upper part 101 firmly, or alternatively can be opened to release the body 1 (once more see FIG. 4).

Figure 6:
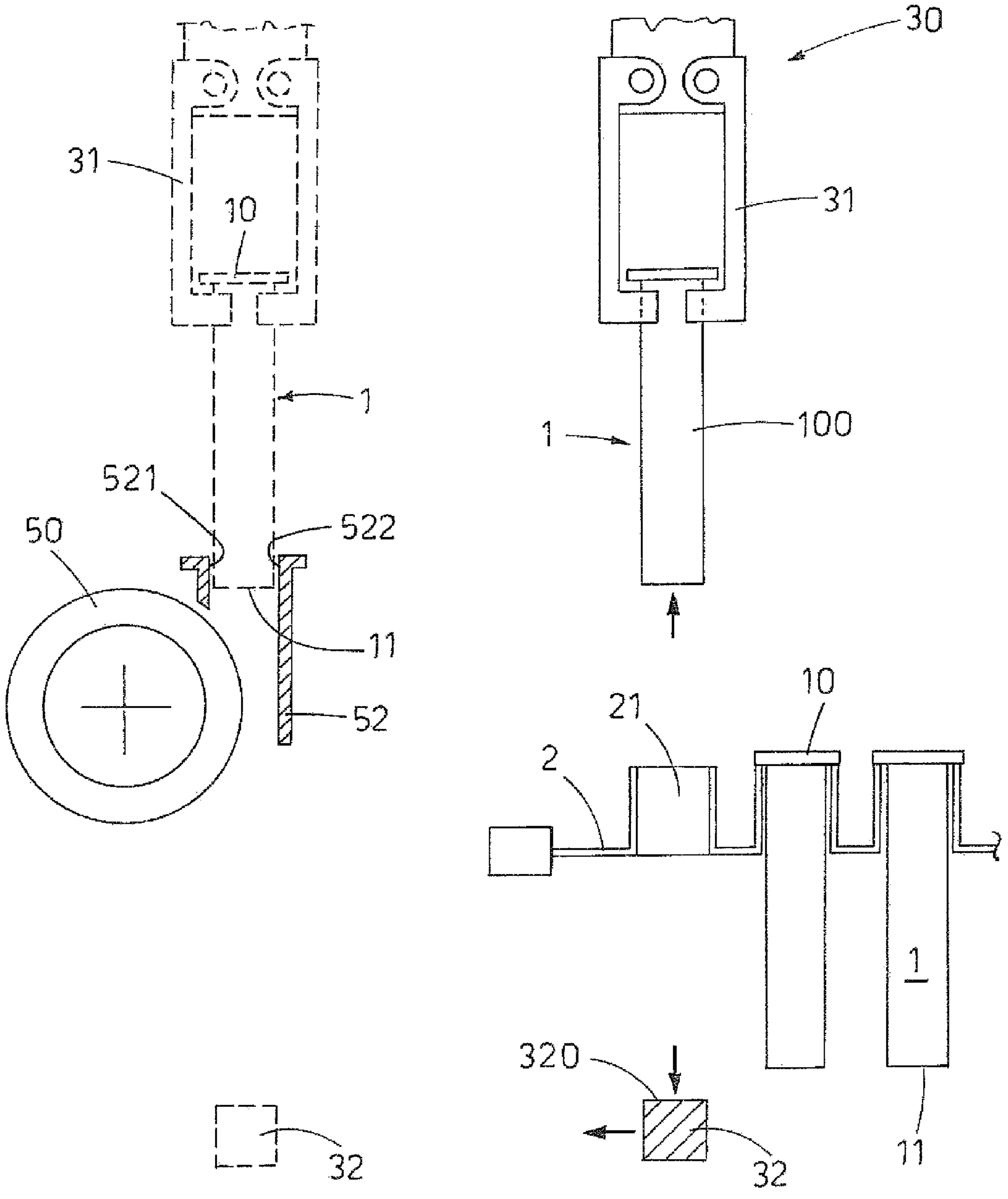
FIG. 6 is a view in vertical section schematically showing the pick-up (or release) cycles of the receptacles from the nest and the positioning (or unloading) thereof in the inserting device.

In this way, extraction of the barrels 1 from the nests 2 is obtained in a safe way, able to ensure that they do not collide with one another, and further, thanks to the use of the pliers 30, the are effectively displaceable, once gripped, without any danger that may fall and break (see FIG. 6).

In a particular aspect of the pick-up means 3, comprised only for the case of barrels 1 presented in nests 2, and in detail of the plurality of pliers 30 (shown in its entirety also in FIGS. 1A 1B), the pair of jaws 31 of each pliers 30 is arrangeable vertically above the barrels 1 to be lifted from the nest 2, with the free ends of each pair of jaws 31 being shaped such as to be able to grip the projecting upper part of a barrel 1, once raised, at opposing points situated immediately below the supporting collar 10, and at the same time, they can inferiorly abut the supporting collar 10 itself, so as increase the firmness of the grip thereof.

In practice, as will be more fully explained herein below, each jaw 31 can have an “L”-shape, i.e. a bend near the lower free end, such as to define a lower horizontal portion, the end of which faces the end of the other jaw of the pair and is destined to encounter the lateral wall 100 of the barrel 1 that it grips, such that the lower horizontal portion supports it resting on the supporting collar 10 thereof (see also FIGS. 3, 4 and 6, for example).

In this way not only is the greatest firmness of grip obtained, but also the smallest size of the pliers 30.

Figure 2:
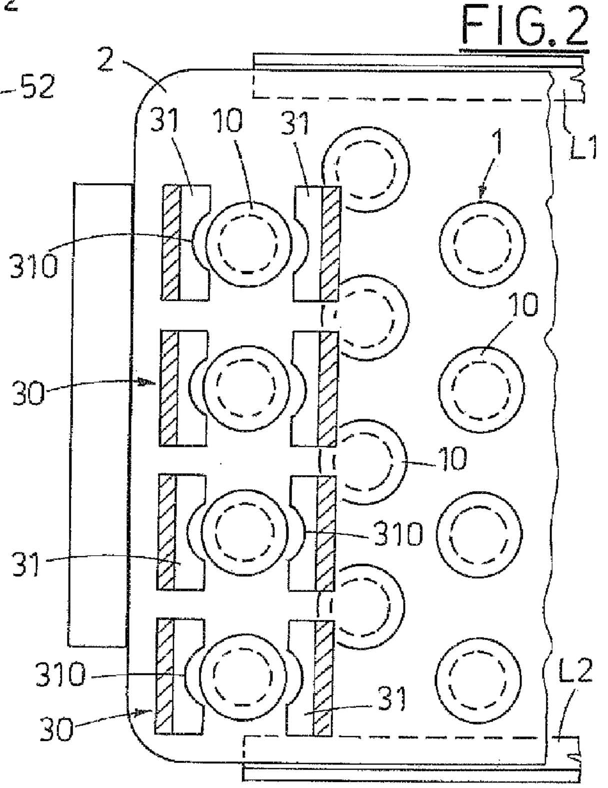
FIG. 2 is a schematic view from above of the collecting means located above a nest.
Figure 5:
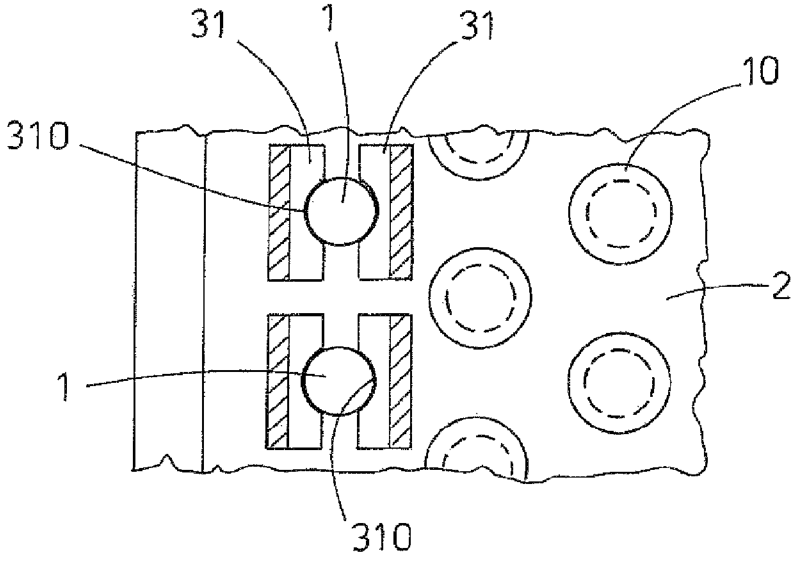
FIG. 5 is a detail of FIG. 2, when the pliers have gripped the receptacles already raised from the nest.

In a preferred aspect, also illustrated in FIGS. 2 and 5, both in the case of containers for recipients 1 comprising nests 2 and in the case of containers comprising trays 20, each jaw 31 of each pair can have a gripping section 310, facing the gripping section 310 of the other jaw 31 of the pair, and having a complementary shape to the shape of the lateral wall 100 of the barrel 1.

In the case of receptacles including trays 20, described above in detail, the invention can comprise an embodiment of the apparatus A (to which FIGS. 12A and 12B schematically refer) in which:

each pliers 30 comprises a pair of jaws 31 dimensioned such as to insert in a housing 201 for gripping a receptacle 1;

the displacing means 4 comprises a rotating device connected to the plurality of pliers 30 so as to be able to rotate (FIG. 12A) the pliers 30 such as to vertically arrange the receptacles 1 taken from the plurality of pliers 30, once extracted from the relative seatings 210 of the tray 20.

For example, the rotating device can be formed by a connected motor inserted in an operating head 33, included in the displacing means 4, which supports the whole row of 3 pliers or other equivalent devices known to the expert person in the field of mechanical engineering and the like.

Not infrequently, as is well known, the seatings of trays 201 extend laterally such as to create, on the side of each housed receptacle 1, an undercut 211, i.e. an empty space, for facilitating gripping and removal of the receptacles 1 (as shown in FIG. 12B).

In this case, each jaw 31 of the pliers 30 can be dimensioned such as to fit into the lateral undercut 201 break 211 so that the pliers 30 can grip a respective receptacle 1 by clamping the lateral wall 100 thereof.

This embodiment can advantageously enable using the apparatus A for transferring receptacles 1 supplied in trays 2 to packing machines M of a type where the recipients, for example the barrels 1 for syringes, are presented in a vertical arrangement.

Preferably, the plurality of pliers 30 is arranged in a straight line in which the pliers 30 are flanked.

In detail, in a possible version thereof (shown in its entirety in FIG. 1A), the plurality of pliers 30 is formed by two facing plates each comprising a continuous base having with an upper edge rotatingly connected with respect to a horizontal upper axis to the operating head 33 of the pick-up means 3.

Figure 3:
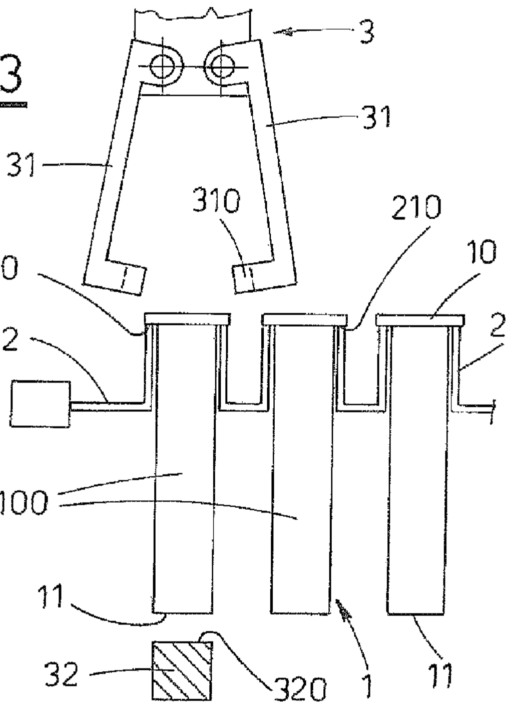
FIG. 3 is a schematic vertical section view of the preceding figure.

Each plate has a free lower edge which forms a plurality of prongs, each of which is L-shaped, curved near the free end (as mentioned above), which free end is shaped so that it can abut the lateral wall 100 of a barrel 1, each prong representing one of the two jaws 31 of the pliers 30, and being arranged facing a prong of the other plate, the reciprocal rotation of the plates (for example the simultaneous rotation in opposite directions, clockwise and anticlockwise) producing either the opening or closing of all the pliers 30 simultaneously (see FIGS. 3 and 4, for example).

In practice, seen from the side or in vertical section, the pairs of jaws 31 have a "L"-shaped profile of the and its mirror image or an "L" and a symmetrical projection thereof, with respect to a vertical axis.

According to a particular version, the above-mentioned displacing means transport 4 includes a robot 400, of well-known type and serving to support and move an object in different points of space.

Several types of robots of this type are known per se, but none in combination with other aspects of the apparatus A.

The robot 400 preferably comprises:

a bearing body 40 destined to oscillate between loading positions thereof, by a flank of the container 2, 20 (which in particular can be located in the pick-up position P), and an unloading position thereof, in proximity of the inserting device 5, a guide 41 for constraining oscillation of the bearing body 40, a motor (not illustrated) for displacing the bearing body 40 along the guide 41 or for halting the bearing body 40 at any position along the guide 41; and a support arm 42 solidly mounted to the bearing body 40, on which support arm 42 the plurality of pliers 30 is mounted, the support arm 42 being movable such as to displace the pliers 30 along two Cartesian axes of a vertical plane.

The support arms 42 of the type described are known per se but not in combination with other aspects of the displacement means 4 and even less with the additional aspects mentioned and still to be described of the apparatus A.

In detail, according to this particular version, the bearing body 40 of the robot 400, when in the loading positions, is arranged with respect to the container 2, 20, such that the support arm 42 can raise the pliers 30, once they have gripped the vessels 1, such as to extract them from the container 2, 20.

Further, the bearing body 40, when in the unloading position, is arranged, with respect to the insertion device 5, so that the support arm 42 can lower the pliers 30 that bear the receptacles 1 such that the receptacles can be inserted in respective movable seatings 52 of the inserting device 5.

Still more specifically, the guide 41 is sufficiently long to enable the bearing body 40, activated by the above-mentioned motor, to be arranged in a plurality of positions flanking the nest 2, in each of which positions the plurality of pliers 30 is activatable in use to take a given row of receptacles 1 in the container 2, 20.

This allows the robot 400, as will be more fully explained below, to perform a succession of pick-up and release cycles each of which collects an entire row of receptacles from the receptacle 1 and 2, releases it in delivery to the inserting device 5, until, after a certain number of cycles, receptacle is completely empties of the receptacles 1 and can be discarded (in the manner explained below).

According to a preferred constructional aspect, the robot 4 guide comprises a straight guide 41 for slidably supporting the bearing body 40 such that it runs only along the longitudinal development of the guide 41.

If a receptacle comprises a nest 2, the robot 400 can also be associated with a pusher organ 34 (shown only in FIG. 1A) solidly mounted with the bearing body 40 and inferiorly fixed to the pusher element 32, activatable to cause vertical oscillation of the pusher element 32.

The pusher element 32 is mounted on the pusher organ 34 such that the upper abutting surface 320 thereof is vertically underlying the plurality of pliers 30.

In this case, the bearing body 40, also activated by the motor, is advantageously available in the various loading positions thereof, flanked to the nest 2, in each of which loading positions the pusher element 32 and the plurality of pliers 30 are arranged respectively below and above one of the rows of housings 21 of the nest 2. The pusher organ 34 may comprise a jack, a linear actuator or other equivalent known device.

In particular, the pusher element 32 may include a rod 32 or a plate having an upper abutting surface 320 that is horizontal and mounted such that it lies in a common vertical plane with the plurality of pliers 30 side by side.

The robot 4 also preferably includes an operating head 33 for supporting the pliers 30, which head 33 comprises means for activating the jaws 31 with respect to the axis of rotation thereof (which can also be the common axis of rotation, in the version of FIG. 1A).

The operating head 33 is included in the support arm 42 is integral element, and therefore is solidly constrained to the pusher element 32.

In practice, the above-described robot 400 is able remove the barrels from the nest 2 as specified herein below (and illustrated in FIGS. 2, 3, 4, 5 and 6).

At each pick-up cycle the bearing body 40 is arranged flanked to the nest 2, and the operating head 33 and the pusher element 32 are arranged at the nest 2 such that the row of pliers 30 and the upper abutting surface 320 of the pusher element 32 are substantially coplanar with the row of barrels 1, i.e. are in the same ideal vertical plane.

As previously mentioned, by means of the support arm 42, and the pusher element 32 the plurality of pliers 30 are always instant by instant solidly constrained.

Therefore in whatever position the bearing body 40 moves or stops at along the guide 41 of the guide, there will always be the certainty of coplanarity between the pliers 30 and the upper abutting surface 320.

It is clear that, for reasons of constructional simplicity, the nest 2 can be made to arrive at the point of collection, with its parallel rows of housings 21 perpendicular to the guide 41 of the guide (see FIG. 1B), such that the coplanar condition mentioned is obtained simply by providing that the rod element 32 and the pusher line of pliers 30 are perpendicular to the guide 41.

After the bearing body 40 has been arranged in the described way, the rod element 32 pushes a row of barrels 1 upwards and, immediately afterwards, the row of pliers 30 grips it.

Thereafter, the row of barrels 1 gripped is removed from the nest 2 by operating the support arm 32 which bears the pliers 30.

The shaft 32 (or plate) is preferably long enough and the pliers 30 are in sufficient numbers such that, in use, the rod 32 (or plate) can push all the barrels 1 of an entire row upwards, and because the pliers 30 can be closed such as to grip each body lifted.

After the barrels have been collected from the nest 2, thanks to the movement of the bearing body 40 along the guide 41, they are taken to the inserting device 5 where they will be inserted in the movable seatings 51, in ways that will be more fully explained herein below.

At this point, the pick up and release cycle begins again from the start and is applied to another row of barrels housed in the nest 2.

In practice, after inserting the collected barrels 1 in the movable seatings 51, also referred-to herein as the release, the robot 400 brings the bearing body 40 back to the nest 2, though in a loading position that is different from the position of the preceding load cycle, i.e. next to a row of housed barrels 1 yet to be housed.

When, after a given number of repeated cycles, which in practice is equal to the parallel rows of housings 21 of the nest 2, the nest 2 is completely empty, it is discarded (or unloaded) in the ways specified below.

In a preferred aspect of the apparatus A, which maximizes efficiency while minimizing design and construction costs, the pliers 30 are equidistantly spaced in their row, i.e. the distance between any two consecutive pliers 30 in a row is always the same, and the housings 21, 210 are equally spaced in the corresponding row, in the same way as the pliers 30, the pliers 30 being at least as many in number as the housings 21, 210 in a row, and the pitch between two consecutive pliers 30 of the row being the same as that between two consecutive quarters 21, 210 such that two receptacles 1 in any one row are the same distance both when housed in a row of the container 2, and when gripped by the row of the plurality of pliers 30.

It is known that robots 400 already in use in this technical field can move objects in such a way that they always remain parallel to themselves.

In this case, the plurality of pliers 30 can be supported and moved such that it is always parallel to itself, with the pliers 30 arranged in a horizontal row.

This facilitates the advantageous follow-mode inserting method, during each release (or inserting) cycle, which is described below.

First, movable seatings 51 of the directing device 5 are preferably arranged in single file, are movable along the longitudinal development of the same single file and are constantly equally spaced to one another, in the sense that the distance between two consecutive locations is the same whichever seatings are considered.

Further, the pitch between two consecutive movable seatings can correspond to a pitch between two positions of the receptacles 1 of a row when taken from the row of pliers 30, such that the distance between two consecutive receptacles 1 in the relative row is the same both when they are inserted in the movable seatings 51 and when they are picked up by the pliers 30.

In use, the movable seatings 51 can be moved continuously (preferably at constant speed) and, once the bearing body 40 of the robot 400 has been brought into the release position, the two-Cartesian-axis support arm 42 is activated such that the plurality of pliers 30 inserts the receptacles 1 in movable seatings 51 in following-mode, while the pliers 30 move, up until the pliers 30 are allowed to open in order to release the receptacles which are then housed in their movable seatings 51.

In the preferred embodiment of the invention, the insertion device 5 comprises an Archimedes screw 50 rotatable around a central rotation axis passing through the inlet I of the packing machine M, the screw 5 having, at a lateral periphery thereof, a helical groove 500 winding around the central axis, which groove 500 is of such a size as to accommodate a barrel 1 positioned vertically, abutting a lateral wall 10 joining the bottom 11 to the support collar 10.

In this case, the inserting device 5 also comprises a straight support and guide element 52 for slidingly restingly receiving the support collars 10 of the barrels 1, once housed in the inserting device 5, such that the barrels 1 are supported by the support element 52.

The support element 52 is positionable parallel to the rotation axis of the screw 50 and is arrangeable with respect thereto such that the groove 500 defines, together with the support element 52, the above-mentioned plurality of movable seatings 51, arranged in single file along the longitudinal development of the cochlea 50, each barrel 1 being housable in each of the movable seatings 51, located in the groove and resting on the straight element 52, each movable seating 51 moving along the longitudinal development of the screw 50 when it is activated in rotation.

Figure 7:
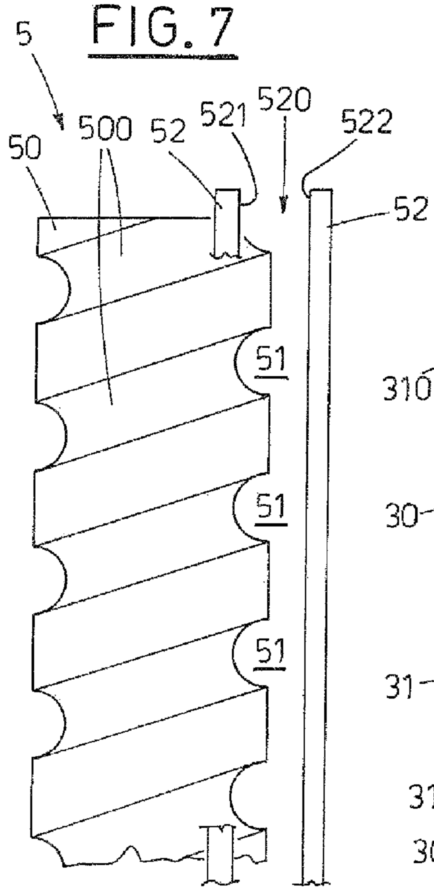
FIG. 7 is a schematic view, partially in cross section, of the inserting device.
Figure 8:
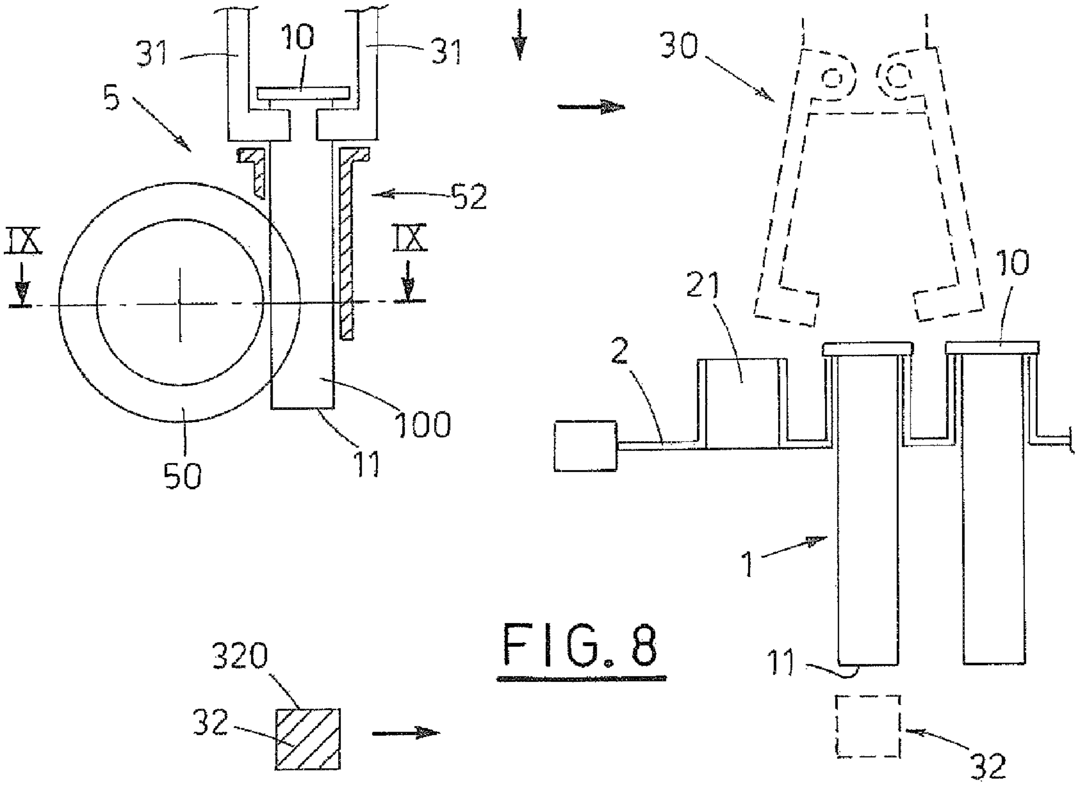
FIG. 8 is the view of FIG. 6 illustrating the insertion of receptacles in movable seatings of the inserting device and the return cycle of the pick-up means.

In detail, as shown in FIGS. 6 and 7 for example, a straight passage 520 is afforded in the guide and support element 52, which straight passage 520 is parallel to the axis of symmetry of the screw 50, defined by two lateral edges 521, 52 facing one another, the straight passage 520 being arranged above the screw 50 and being of such a width that barrels 1 can be freely inserted between the lateral edges 521, 522 only up the relative support collars 10, such that two opposite portions of each collar 10 are each restingly received at a different edge 521, 522 of the passage 520 of the guide and support element 52 (see FIGS. 6 and 8).

The passage 520 can be simply defined by flanking two parallel horizontal plates at a certain reciprocal distance, with respective facing edges that thus define the passage 520.

In the following we describe a particular aspect of the apparatus A, schematically illustrated in FIGS. 10 and 11, relative to the removal of the nest 2, which is in the pickup position P, once it has been emptied of the barrels 1.

The pickup position P can advantageously be comprised in a terminal portion of the conveyor line L vertically lowerable to bring the empty nest 2, which rests above, to an underlying level.

When it is at this underlying level, the nest is placed 2 in the same horizontal plane as the rod 32 of the pusher element.

Then the robot 400 can be activated so that the bearing body 40 slides along the guides, bringing the rod 32 to push the nest 2 which is then removed from the lowerable terminal portion of the conveyor line L and sent into an unloading zone (not described in detail as it can be any one of the known types).

The terminal portion is then vertically raised and the conveyor line L is activated to bring another nest 2 to rest thereon.

The above has been described by way of non-limiting example, and any constructional variants are understood to fall within the ambit of protection of the technical solution, as claimed herein below.

What is claimed is:

1. A method for transferring a plurality of tubular receptacles made of a fragile material from containers in which the plurality of receptacles are housable separately, to a packing machine, the method comprising:

moving each container by a conveyor line towards the packing machine, each container being a tray having a plurality of receptacle housings which are open, superiorly accessible and suitable for singly housing horizontally-arranged receptacles, the receptacles being separated from one another and arranged in the trays in parallel lines;

supplying the trays along the conveyor line to a pickup position in proximity of an inlet of the packing machine;

stopping the trays during each receptacle pick-up operation;

collecting the plurality of receptacles from a parallel line of a tray, by vertically and contemporaneously lifting all of the plurality of horizontally arranged receptacles from the respective housings, picking up the receptacles from the tray, and maintaining the plurality of picked up receptacles in a horizontal arrangement separated from one another;

taking the plurality of horizontally arranged picked up receptacles to the inlet of the packing machine arranged in a line, separated from one another, the line constituting said predefined formation;

rotating the line of horizontally arranged picked up receptacles so that all the receptacles are arranged vertically, and;

locating the rotated line of receptacles arranged in the vertical line formation at the inlet of the packing machine, maintaining the vertical line of receptacles separated from one another;

bringing the collected and arranged vertical line of receptacles into the packing machine, maintaining the receptacles in the vertical line separated from one another, by translating the vertical line of receptacles longitudinally so as to bring the receptacles one at a time into the packing machine, constantly keeping the receptacles during the translation separated from one another, the packing machine receiving the vertical line of collected and arranged receptacles therein for processing;

repeating the collecting, taking, rotating, locating and bringing steps cyclically to each of the parallel lines of the receptacles housed in the tray, wherein the bringing step has a duration which is at most equal to the sum of the durations of collecting, taking and locating steps, so that in a cycle, the bringing step for a line of receptacles is completed during the collecting, taking, rotating and locating steps applied to a further line of receptacles in a following cycle; and wherein, after all the receptacles housed in the tray located in the pick-up position have been collected, the tray is removed from the conveyor line and a further tray is advanced to the pick-up position, and repeating the steps of the method.

2. The method of claim 1, wherein the receptacles are barrels for syringes, suitable for containing a liquid, each barrel having an upper support collar, formed at a rim of a respective mouth thereof, and each barrel having a bottom opposite the mouth, wherein after the rotating step, the barrels are arranged vertically and oriented with each support collar and mouth located above the bottom.

3. The method of claim 1, further comprising:

providing a plurality of movable seatings at the packing machine inlet, each movable seating adapted for housing a relative receptacle for bringing the receptacle to the packing machine inlet;

arranging the mobile seatings with respect to one another such that the receptacles inserted in the movable seatings are maintained in the predefined formation separated from one another;

continuously moving the movable seatings;

inserting the receptacles into the movable seatings in a following mode as the movable seatings are moving.

4. An apparatus for transferring a plurality of tubular receptacles made of a fragile material, the receptacles being barrels for syringes, suitable for containing doses of medicinal substances, from containers having nests for accepting the barrels, each nest having a plurality of vertical through-cavities, each through-cavity vertically housing a respective barrel, a support collar of the barrel rested upon an upper surface of the through-cavity, a bottom of the barrel, located opposite the support collar, projecting below the nest, to a packing machine having an inlet for receiving the barrels, the apparatus comprising:

at least one pick-up device for picking up a plurality of barrels from a nest and for releasing the barrels, the pick-up device configured to maintain the barrels separated while picking the barrels up and after picking the barrels up, the pick-up device being a plurality of pliers, each pliers having a pair of jaws, positionable above the nest, each pliers being closable for singly gripping a barrel, and openable to release the barrel, the pliers being arranged at a reciprocal distance such that the barrels, while being gripped and once gripped by a respective pliers, are maintained separated from one another;

at least one inserting device provided at the packing machine inlet for delivering the barrels extracted from the nest to the packing machine inlet, the inserting device having a plurality of movable seatings arranged separated from one another, each movable seating receiving and housing a barrel, the plurality of movable seatings arranged in a predefined configuration for separating the barrels from one another, the inserting device being activatable to move the movable seatings with the barrels housed therein to the packing machine inlet;

displacing means for supporting the pick-up device and displacing the pick-up device, so that the barrels are extracted from the nest and are taken to the inserting device, the displacing means being activatable to move the pick-up device to the inserting device and to move the pick-up device for introducing the barrels into the movable seatings of the inserting device, the barrels being then released and housed in the movable seatings;

wherein the pick-up device has at least one pusher element positionable below the nest and having an upper abutting surface, the pusher element being oscillatable vertically for performing an upwards run, the upper surface of the pusher element pushing upwards the bottoms of the barrels of a line of barrels in the nest, upper parts of the pushed barrels, including the support collar, projected upwardly relative to the housings, and therefore of the nest;

the plurality of pliers being positionable above the nest, each pair of jaws being closable so as to solidly grip the upper projecting part of each barrel pushed upwards by the pusher element beneath the support collars thereof;

wherein the displacing means comprise a robot for supporting and moving the plurality of pliers in space, the robot having a bearing body oscillatable between a loading position thereof, located by a flank of the nest which houses the barrels to be picked up, and an unloading position thereof in proximity of the inserting device;

a guide for constraining the oscillation of the bearing body;

a motor for displacing the bearing body along the guide or for stopping the bearing body in any position therealong;

a support arm mounted solidly to the bearing body, on which support arm the plurality of pliers are mounted, the support arm being movable in order to displace the pliers along two Cartesian axes of a vertical plane;

the bearing body, when in the loading position, being arranged with respect to the barrels such that the support arm can lift the pliers, once the pliers have gripped the barrels, so as to extract the barrels from the nests, and the bearing body, when in the unloading position, being further arranged with respect to the inserting device such that the arm can lower the pliers which bear the barrels for inserting the barrels in respective movable seatings of the inserting device; and, wherein the robot has a pusher organ mounted solidly to the bearing body, fixed below the pusher element, and activatable to cause a vertical oscillation of the pusher element, the pusher element being mounted on the pusher organ such that the upper abutting surface is vertically below the plurality of pliers.

5. The apparatus of the claim 4, wherein when the barrels are arranged in parallel lines in the nest, the bearing body being movable along the guide for arrangement in several loading positions located along the flank of the nest, in each loading position, the pusher element and the plurality of pliers being arranged respectively below and above one parallel line of housings of the nest.

6. The apparatus of claim 4, wherein the plurality of pliers are formed by two facing plates, each plate having a continuous base, an upper edge constrained rotatingly to a remaining part of the pick-up device, and a free lower edge which forms a plurality of tines, each tine being curved in an L shape in proximity of a free end thereof, conformed to abut a lateral wall of a barrel, each tine constituting one of the two jaws of each pliers, and being arranged facing a tine of the facing plate, reciprocal rotation of the facing plates alternatively producing an opening or a closing of all the pliers contemporaneously.

7. The apparatus of claim 4, wherein the inserting device includes an Archimedes screw rotatable about a central rotation axis which passes through the packing machine inlet, the Archimedes screw having, at a lateral periphery thereof, a helical channel arranged about the central axis, which channel is dimensioned so as to house a barrel arranged vertically, the channel abutting a lateral wall thereof.

8. The apparatus of claim 7, wherein the inserting device has a straight rest and guide element for restingly slidably receiving the support collars thereon, the barrels being supported by the straight rest and guide element, the straight rest and guide element being positionable parallel to the rotation axis of the Archimedes screw and with respect thereto such that the channel defines, together with the straight rest and guide element, said plurality of movable seatings, arranged in the line, along a longitudinal development of the Archimedes screw, each barrel being housable in each of the movable seatings being accommodated by the channel and resting on the straight rest and guide element, each movable seating moving along the longitudinal development of the Archimedes screw when the Archimedes screw is rotated.

9. The apparatus of claim 8, wherein the straight rest and guide element includes a straight passage positioned parallel to an axis of symmetry of the Archimedes screw, the straight passage defined by two lateral edges facing one another, the straight passage being arranged above the Archimedes screw and having a width sufficient for freely receiving the barrels inserted between the lateral edges thereof, the support collars restingly received on the lateral edges flanking and defining the straight passage.

10. An apparatus for transferring a plurality of tubular receptacles made of a fragile material from containers, each container being a tray for the receptacles, the tray having pluralities of open housings, superiorly accessible and able to singly house respective receptacles horizontally arranged therein such that the receptacles are separated from one another, to a packing machine having an inlet for receiving the receptacles, the apparatus comprising:

at least one pick-up device for picking up a plurality of receptacles from the tray and releasing the receptacles, the pick-up device configured to maintain the receptacles separated while picking up the receptacles and after the receptacles are picked-up, the pick-up device having a plurality of pliers, each pliers having a pair of jaws, positionable above the tray, each pliers being closable for singly gripping a receptacle and openable for releasing the receptacle, the pliers being arranged at a reciprocal distance such that the receptacles, while being gripped and once gripped by a respective pliers, are maintained separated from one another, at least one inserting device provided at the inlet of the packing machine, for bringing the receptacles extracted from the tray to the packing machine inlet, the inserting device having a plurality of movable seatings arranged separated from one another, each movable seating receiving and housing a receptacle, the plurality of movable seatings arranged for housing the receptacles in a predefined configuration in which the receptacles are separated from one another, the inserting device being activatable to move the movable seatings, with the receptacles housed therein, the packing machine inlet and a displacing means for supporting the pick-up device and displacing the pick-up device, once the receptacles have been picked up, so that the picked-up receptacles are extracted from the tray and taken to the inserting device, the displacing means being activatable to displace the pick-up device, after the receptacles are picked up, to the inserting device and to move the pick-up device so that the receptacles are introduced into the movable seatings, whereby the receptacles are received and housed in the movable seatings, each pliers having a pair of jaws dimensioned for inserting into a housing for gripping a receptacle;

the displacing means being a robot for supporting and moving the plurality of pliers in space, and having a rotating device connected to the plurality of pliers for rotating the pliers to vertically arrange the picked up receptacles, extracted from the relative housings of the tray.

11. The apparatus of claim 10, wherein the plurality of pliers are formed by two facing plates, each plate having a continuous base, an upper edge constrained rotatingly to a remaining part of the pick-up device, and a free lower edge which forms a plurality of tines, each tine being curved in an L shape in proximity of a free end thereof, conformed to abut a lateral wall of a receptacle, each tine constituting one of the two jaws of each pliers, and being arranged facing a tine of the facing plate, reciprocal rotation of the facing plates alternatively producing an opening or a closing of all the pliers contemporaneously.

12. The apparatus of claim 10, wherein the inserting device includes an Archimedes screw rotatable about a central rotation axis which passes through the packing machine inlet, the Archimedes screw having, at a lateral periphery thereof, a helical channel arranged about the central axis, which channel is dimensioned so as to house a receptacle arranged vertically, the channel abutting a lateral wall thereof.

13. The apparatus of claim 12, wherein the receptacles each have an upper support collar formed at a rim of a respective mouth thereof, each receptacle having a bottom opposite the mouth, the lateral wall joining the bottom to the support collar, the inserting device having a straight rest and guide element for restingly slidably receiving the support collars thereon, the receptacles being supported by the straight rest and guide element, the straight rest and guide element being positionable parallel to the rotation axis of the Archimedes screw and with respect thereto such that the channel defines, together with the straight rest and guide element, said plurality of movable seatings, arranged in the line, along a longitudinal development of the Archimedes screw, each receptacle being housable in each of the movable seatings being accommodated by the channel and resting on the straight rest and guide element, each movable seating moving along the longitudinal development of the Archimedes screw when the Archimedes screw is rotated.

14. The apparatus of claim 13, wherein the straight rest and guide element includes a straight passage positioned parallel to an axis of symmetry of the Archimedes screw, the straight passage defined by two lateral edges facing one another, the straight passage being arranged above the Archimedes screw and having a width sufficient for freely receiving the receptacles inserted between the lateral edges thereof, the support collars restingly received on the lateral edges flanking and defining the straight passage.

* * * * *